(12) United States Patent
Elton

(10) Patent No.: US 11,298,509 B2
(45) Date of Patent: Apr. 12, 2022

(54) RADIOPAQUE GUIDEWIRE TO FACILITATE CATHETER ALIGNMENT

(71) Applicant: CLEARSTREAM TECHNOLOGIES LIMITED, Enniscorthy (IE)

(72) Inventor: Richard K. Elton, Queensbury, NY (US)

(73) Assignee: CLEARSTREAM TECHNOLOGIES LIMITED, Enniscorthy (IE)

( * ) Notice: Subject to any disclaimer, the term of this patent is extended or adjusted under 35 U.S.C. 154(b) by 1463 days.

(21) Appl. No.: 14/758,617

(22) PCT Filed: Dec. 31, 2013

(86) PCT No.: PCT/IB2013/002958
§ 371 (c)(1),
(2) Date: Jun. 30, 2015

(87) PCT Pub. No.: WO2014/102599
PCT Pub. Date: Jul. 3, 2014

(65) Prior Publication Data
US 2015/0335867 A1      Nov. 26, 2015

Related U.S. Application Data

(60) Provisional application No. 61/747,431, filed on Dec. 31, 2012.

(51) Int. Cl.
*A61M 25/09* (2006.01)
*A61M 25/01* (2006.01)
(Continued)

(52) U.S. Cl.
CPC ........ *A61M 25/09* (2013.01); *A61M 25/0108* (2013.01); *A61M 25/104* (2013.01);
(Continued)

(58) Field of Classification Search
CPC ........ A61M 2025/09166; A61M 25/10; A61M 2025/1079; A61M 2025/105;
(Continued)

(56) References Cited

U.S. PATENT DOCUMENTS

| | | |
|---|---|---|
| 4,664,113 A | 5/1987 | Frisbie et al. |
| 4,838,268 A | 6/1989 | Keith et al. |

(Continued)

FOREIGN PATENT DOCUMENTS

| | | |
|---|---|---|
| EP | 0879614 A1 | 11/1998 |
| GB | 2355797 A | 5/2001 |

(Continued)

OTHER PUBLICATIONS

Terada, et al.; "Standard Technique of PTA/stenting for Atherosclerotic Intracranial Arterial Stenosis"; Wakayama Medical University; Japan; 2004.

*Primary Examiner* — Nathan R Price
*Assistant Examiner* — Weng Lee
(74) *Attorney, Agent, or Firm* — Dickinson Wright PLLC; Andrew D. Dorisio

(57) ABSTRACT

An apparatus for treating a treatment area in the vasculature using a catheter having a balloon. The apparatus comprises a guidewire for guiding the balloon to the treatment area, said guidewire including one or more radiopaque markings arranged for corresponding to the treatment area. Related aspects and methods are also disclosed.

14 Claims, 9 Drawing Sheets

(51) Int. Cl.
*A61M 25/10* (2013.01)
*A61M 25/00* (2006.01)

(52) U.S. Cl.
CPC ............... *A61M 2025/0008* (2013.01); *A61M 2025/09166* (2013.01); *A61M 2025/105* (2013.01)

(58) Field of Classification Search
CPC .... A61M 25/0108; A61M 2025/09125; A61M 2025/09133; A61M 10/10; A61M 10/0108
See application file for complete search history.

(56) References Cited

U.S. PATENT DOCUMENTS

| | | | |
|---|---|---|---|
| 4,844,092 A | 7/1989 | Rydell et al. | |
| 5,209,730 A * | 5/1993 | Sullivan | A61M 25/0108 600/434 |
| 5,217,435 A | 6/1993 | Kring | |
| 5,265,622 A | 11/1993 | Barbere | |
| 5,300,048 A * | 4/1994 | Drewes, Jr. | A61M 25/0108 600/435 |
| 5,364,354 A | 11/1994 | Walker et al. | |
| 5,379,779 A * | 1/1995 | Rowland | A61M 25/09 600/585 |
| 5,383,890 A * | 1/1995 | Miraki | A61M 25/104 604/913 |
| 5,460,185 A | 10/1995 | Johnson et al. | |
| 5,499,632 A | 3/1996 | Hill, III et al. | |
| 5,836,306 A | 11/1998 | Duane et al. | |
| 5,836,892 A | 11/1998 | Lorenzo | |
| 5,851,210 A | 12/1998 | Torossian | |
| 5,860,923 A | 1/1999 | Lenker et al. | |
| 6,078,832 A | 6/2000 | Lenker et al. | |
| 6,179,788 B1 | 1/2001 | Sullivan | |
| 7,033,325 B1 * | 4/2006 | Sullivan | A61M 25/09 600/434 |
| 7,303,798 B2 | 12/2007 | Bavaro et al. | |
| 7,706,861 B2 | 4/2010 | Windheuser et al. | |
| 7,833,597 B2 | 11/2010 | Bavaro et al. | |
| 8,292,827 B2 | 10/2012 | Musbach et al. | |
| 2004/0093011 A1 | 5/2004 | Vrba | |
| 2005/0064223 A1 * | 3/2005 | Bavaro | A61B 5/1076 428/615 |
| 2005/0215950 A1 * | 9/2005 | Burgmeier | A61M 25/10 604/103.1 |
| 2008/0300610 A1 | 12/2008 | Chambers | |
| 2009/0181156 A1 * | 7/2009 | Nesbitt | A61L 31/10 427/2.1 |
| 2010/0022917 A1 | 1/2010 | Landowski | |
| 2011/0218520 A1 * | 9/2011 | Andrich | A61M 25/0017 604/544 |

FOREIGN PATENT DOCUMENTS

| | | |
|---|---|---|
| JP | 2004249095 A | 9/2004 |
| JP | 2007020885 A | 2/2007 |
| JP | 2011156115 A | 8/2011 |
| WO | 9819629 A2 | 5/1998 |
| WO | 2007042936 A2 | 4/2007 |
| WO | 2008033929 A2 | 3/2008 |

* cited by examiner

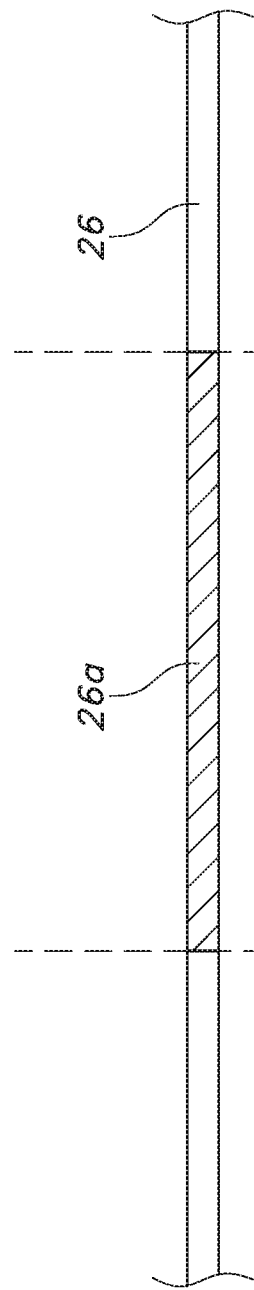
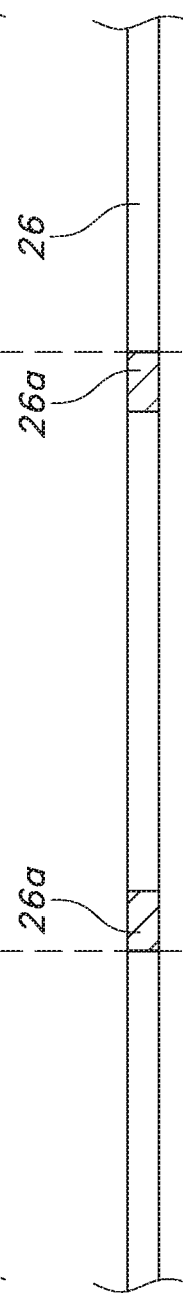
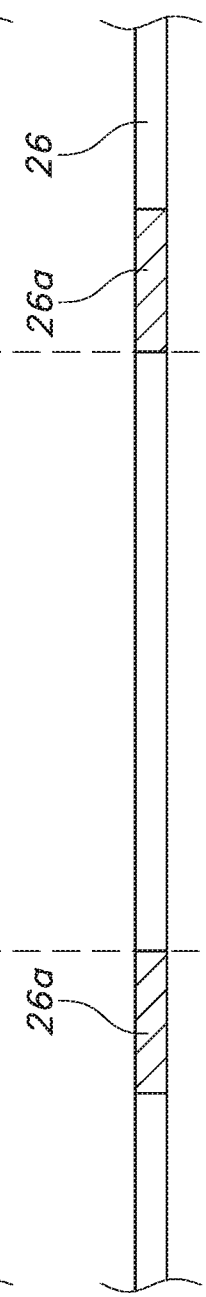
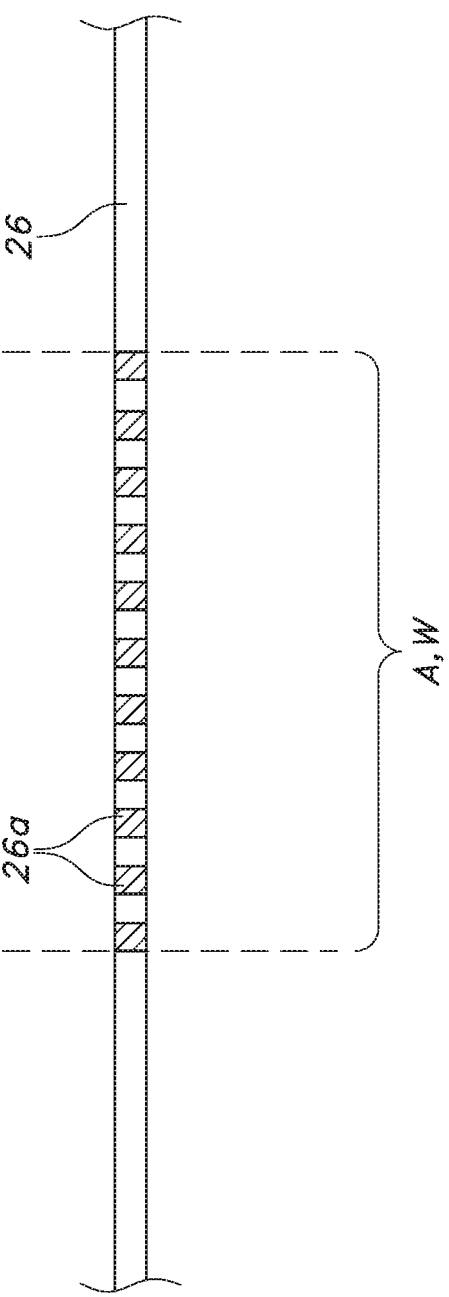
FIG. 7
FIG. 8
FIG. 9
FIG. 10

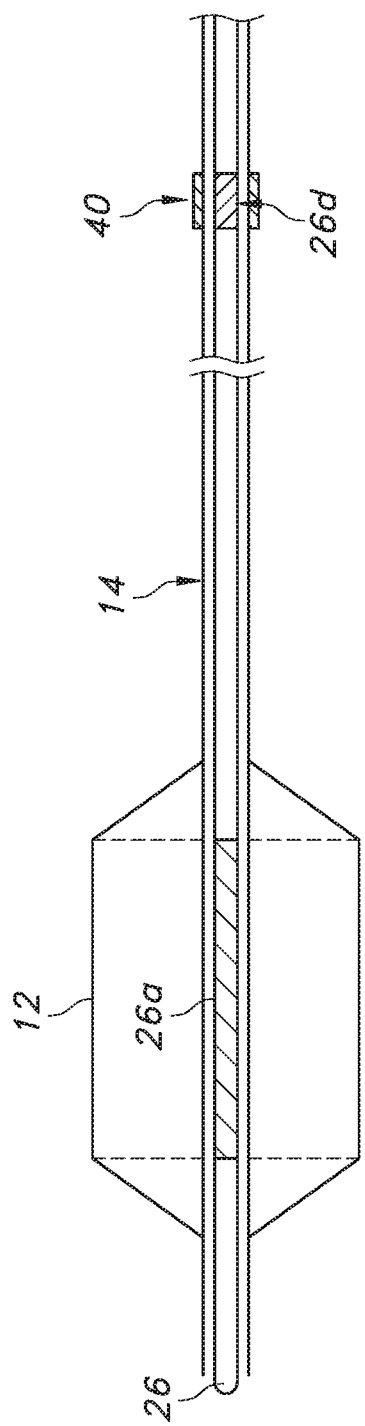
FIG. 13
FIG. 14
FIG. 15

RADIOPAQUE GUIDEWIRE TO FACILITATE CATHETER ALIGNMENT

This application claims the benefit of U.S. Provisional Patent Application Ser. No. 61/747,431, which is incorporated herein by reference.

TECHNICAL FIELD

This disclosure relates generally to interventional medical procedures, such as angioplasty, and, more particularly, to a radiopaque guidewire to facilitate the alignment of a catheter.

BACKGROUND OF THE INVENTION

Catheters including balloons are routinely used to resolve or address flow restrictions or perhaps even complete blockages in tubular areas of a body, such as arteries or veins. In many clinical situations, the restrictions are caused by hard solids, such as calcified plaque, and may sometimes involve the use of high pressures to compact such blockages. Commercially available balloons employ complex technology to achieve high pressure requirements without sacrificing the profile of the balloon. Besides high pressure requirements, the balloons should also be resistant to puncture, easy to track and push, and present a low profile, especially when used for angioplasty.

The clinician performing the angioplasty procedure should be able to locate the position of the uninflated balloon with accuracy, so that the balloon will be properly positioned once inflated. This is conventionally accomplished by attaching marker bands on the catheter shaft corresponding to the ends of the balloon working surface. This "working surface" is the surface along the largest diameter portion of the balloon when inflated adapted to contact a calcified plaque (which surface in the case of a balloon having conical or tapering sections at the proximal and distal ends is co-extensive with a generally cylindrical barrel section, and does not include the conical or tapering sections).

However, misalignment of the marker bands during placement along the shaft sometimes results in their failure to correspond precisely to the extent of the working surface. This misalignment may prevent the clinician from accurately identifying the location of the working surface of the balloon during an interventional procedure. Another disadvantage with the use of marker bands is that the band may disrupt the otherwise smooth surface of the catheter shaft over which the band is placed. Bands are typically affixed to the catheter shaft by means of crimping, swaging, or adhesive bonding, or a combination of the above. The result is that the band will often produce a slightly increased profile compared to the adjacent smooth shaft. The inside surface of the balloon contacts this band and its raised profile. It is possible, and common, that the pressure and handling encountered during balloon folding and wrapping (to form the balloon into it's final configuration for packaging) can cause abrasion on the inside surface of the balloon. This abrasion can weaken the balloon and cause it to burst prematurely when deployed and pressurized.

Also, when successive intravascular interventions are made, such as during a pre-dilatation using a first catheter followed by dilatation using a second catheter, the clinician must guess at the location where the pre-dilatation occurred. In either case, this uncertainty may lead to a geographic misalignment, or "miss," of the desired precise contact between the intended treatment area and the working surface of the balloon. It is especially desirable to avoid such an outcome when the balloon is designed to deliver a payload (such as a therapeutic agent (e.g., a drug, such as paclitaxel, rapamycin, heparin and the like), a stent, a stent graft, or a combination of the foregoing) or a working element (such as a cutter, focused force wire, or the like) to a specified location within the vasculature, since a miss may, at a minimum, prolong the procedure (such as, for example, by requiring redeployment of the balloon or the use of another balloon catheter in the case of a drug coated balloon), and possibly result in an inferior outcome if the lesion is not properly treated as a result of the misalignment.

Existing technology known as "rapid exchange," or "RX" for short, uses a guidewire that extends through an opening spaced distally from the proximal end and through the balloon. This guidewire may sometimes include a marker positioned external to the body for measuring the distance from the catheter tip. However, this marker does not in any way relate to the particular length of a treatment area or a working surface of the balloon, and thus cannot aid in resolving the geographic misalignment issue.

Accordingly, a need exists for a manner in which to position a balloon catheter into the vasculature at a treatment area with enhanced accuracy, and also in a manner that is highly repeatable.

SUMMARY OF THE INVENTION

An object of the disclosure is to provide a radiopaque guidewire for aligning with a catheter to help ensure accurate alignment of a treatment with a treatment area.

One aspect of the disclosure relates to an apparatus for treating a treatment area in the vasculature using a catheter having a balloon. The apparatus comprises a guidewire for guiding the balloon to the treatment area. The guidewire includes one or more radiopaque markings arranged for corresponding to the treatment area.

The one or more radiopaque markings may correspond in size or position to the treatment area. The guidewire may include at least two radiopaque markings corresponding to the treatment area. In one possible embodiment, the guidewire includes a proximal marking adapted for aligning with a reference point on the catheter when the one or more radiopaque markings align with the treatment area, the proximal marking preferably being provided so as to be outside of a patient's vasculature when the one or more radiopaque markings align with the treatment area, the proximal marking preferably being visible to the naked eye.

The guidewire may include a second radiopaque marking for aligning with a radiopaque marking on a catheter shaft of the catheter when the working surface of the balloon of the catheter aligns with the first radiopaque marking. The second radiopaque marking on the guidewire for aligning with the radiopaque marking on the cathether shaft may be at a tip of the guidewire, and the corresponding radiopaque marking is at a distal end of the catheter shaft.

A stopper may also be provided. The stopper may be adapted for receiving a proximal portion of the guidewire adjacent to an opening at a proximal end of the catheter. A distal end of the stopper may be adapted for abutting with a face of the catheter adjacent the opening. The stopper may be adapted for positioning in the opening.

One or a plurality of balloon catheters may also be provided in combination with the guidewire. The balloon catheter may include a treatment for treating the treatment area. The treatment may be selected from the group consisting of a drug, a stent, a stent graft, a cutter, a focused force wire, or any combination of the foregoing.

A further aspect of the disclosure pertains to an apparatus for treating a treatment area in the vasculature using a catheter having a balloon including a working surface having a length for engaging the treatment area. The apparatus comprises a guidewire for guiding the balloon to the treatment area, said guidewire including one or more radiopaque markings corresponding to the length of the working surface of the balloon, the correspondence preferably being a correspondence in size.

The guidewire may include at least two radiopaque markings corresponding to the length of the working surface. The guidewire may include a proximal marking adapted for aligning with a reference point when the one or more radiopaque markings align with the treatment area. A stopper may be provided for receiving a proximal portion of the guidewire adjacent to an opening at a proximal end of the catheter, and may have a distal end adapted for abutting with a face of the catheter adjacent the opening or for positioning in the opening.

Still another aspect of the disclosure pertains to a catheter including a distal end supporting a balloon having a working surface and a proximal end. A guidewire is provided for guiding the balloon to the treatment area, said guidewire including one or more radiopaque markings adapted for corresponding to the working surface of the balloon when positioned at the treatment area. The one or more radiopaque markings may correspond in size or position to the working surface. The guidewire may comprise two first radiopaque markings corresponding to the working surface.

The catheter may include a reference point at the distal end, and the guidewire may include a marking for corresponding to the reference point when the one or more radiopaque markings align with the working surface of the balloon. The distal end of the catheter may include a hub having the reference point. A stopper may be adapted for receiving a proximal portion of the guidewire adjacent to an opening at the proximal end of the catheter. The stopper may have a distal end for abutting with a face of the catheter adjacent the opening, or may be adapted for positioning in the opening. The balloon may include a treatment selected from the group consisting of a therapeutic agent, a stent, a stent graft, a cutter, a focused force wire, or any combination of the foregoing.

BRIEF DESCRIPTION OF THE FIGURES

FIGS. 7-10 illustrate various ways in which one or more radiopaque markings may be provided on a guidewire used in an embodiment of the present disclosure.

FIGS. 13-15 show different variations of markings on a guidewire used in an embodiment of the present disclosure.

MODES FOR CARRYING OUT THE INVENTION

The description provided below and in regard to the figures applies to all embodiments unless noted otherwise, and features common to each embodiment are similarly shown and numbered.

Figure 1:
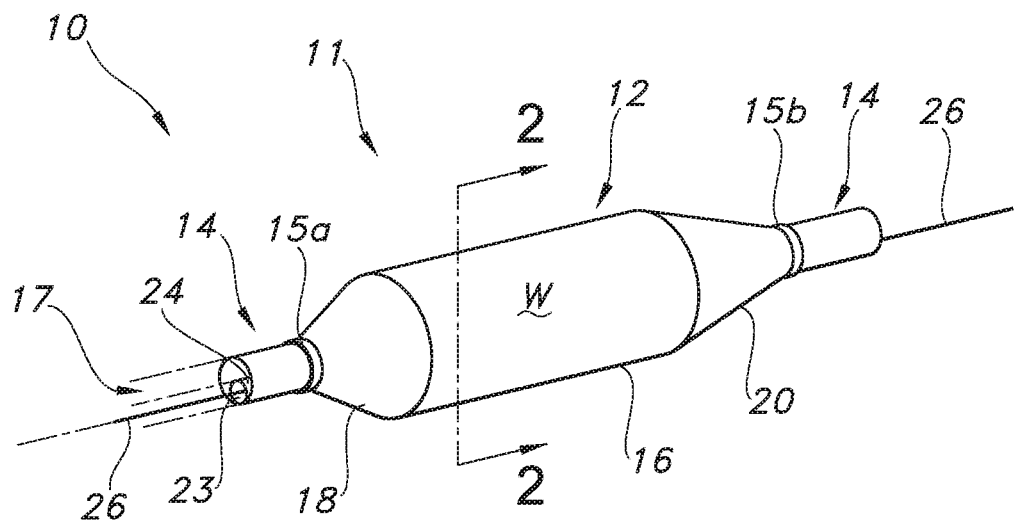
FIGS. 1-3 show an apparatus for angioplasty according to an embodiment of the present disclosure.
Figure 2:
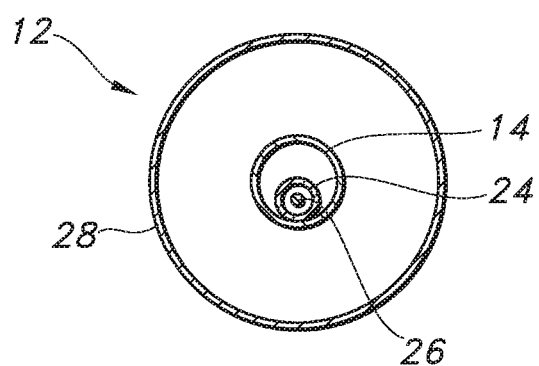
Figure 3:
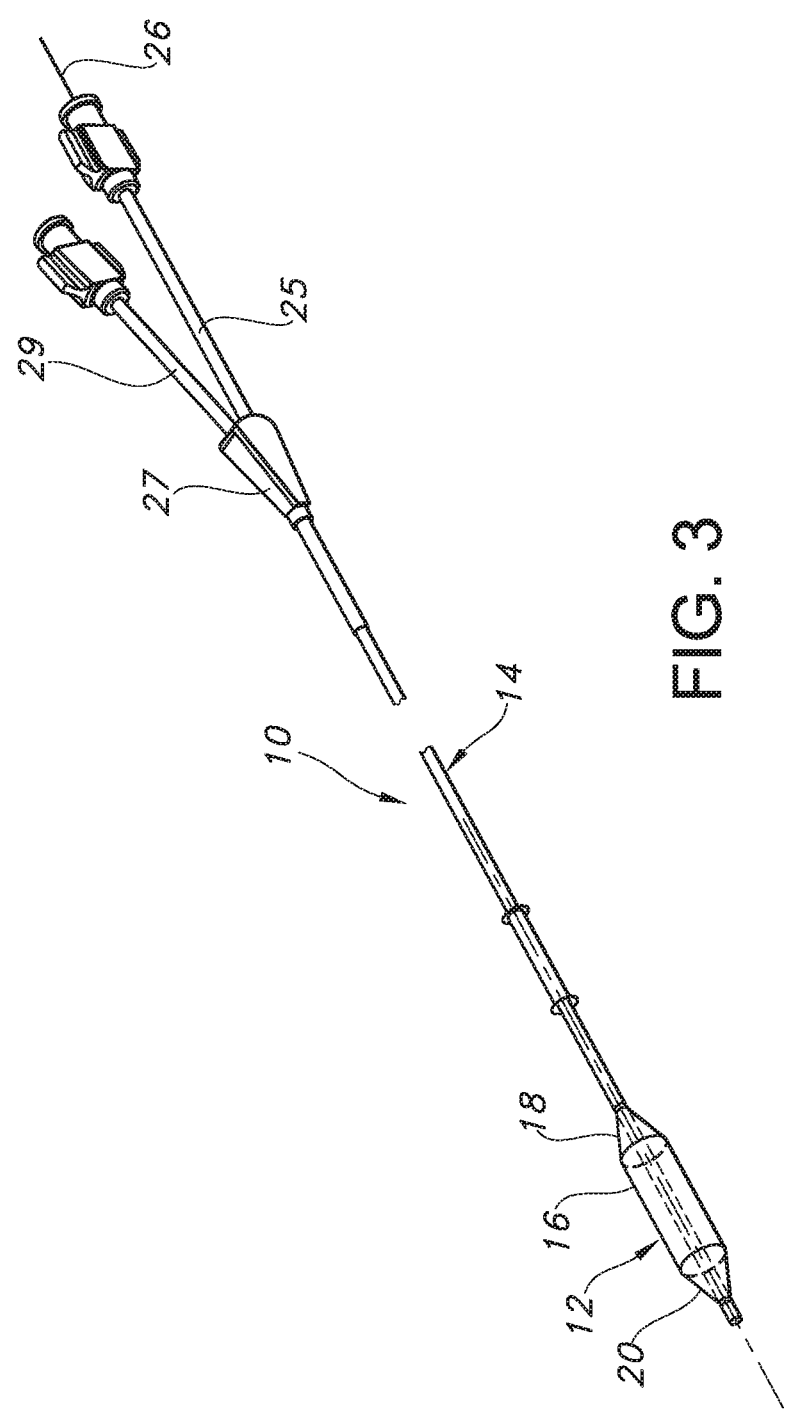

Provided is a catheter 10 having a distal portion 11 with a balloon 12 mounted on a catheter tube 14. Referring to FIGS. 1, 2, and 3, the balloon 12 has an intermediate section 16, or "barrel" having the working surface W, and end sections 18, 20. In one embodiment, the end sections 18, 20 reduce in diameter to join the intermediate section 16 to the catheter tube 14 (and thus sections 18, 20 are generally termed cones or cone sections). The balloon 12 is sealed to catheter tube 14 at balloon ends (proximal 15a and distal 15b) on the end sections 18, 20 to allow the inflation of the balloon 12 via one or more inflation lumens 17 extending within catheter tube 14 and communicating with the interior of the balloon 12. The catheter tube 14 also includes an elongated, tubular shaft 24 forming a guidewire lumen 23 that directs the guidewire 26 through the catheter 10. As illustrated in FIG. 3, this guidewire 26 may be inserted through a first port 25 of a connector 27, or hub, into the lumen 23 to achieve an "over the wire" (OTW) arrangement. A second port 29 may also be associated with catheter 10, such as by way of connector 27, for introducing a fluid (e.g., saline, a contrast agent, or both) into the interior of the balloon 12 via the inflation lumen 17.

Balloon 12 may include a single or multi-layered balloon wall 28. The balloon 12 may be a non-compliant balloon having a balloon wall 28 that maintains its size and shape in one or more directions when the balloon is inflated. The balloon 12 in such case also has a pre-determined surface area that remains constant during and after inflation, also has a pre-determined length and pre-determined circumference that each, or together, remain constant during and after inflation. However, the balloon 12 could be semi-compliant or compliant instead, depending on the particular use. The balloon 12 may also include a treatment, such as a payload (drug, stent, stent graft, or any combination of these items) or a working implement (cutter, focused force wire, or the like) into the vasculature.

Figure 4:
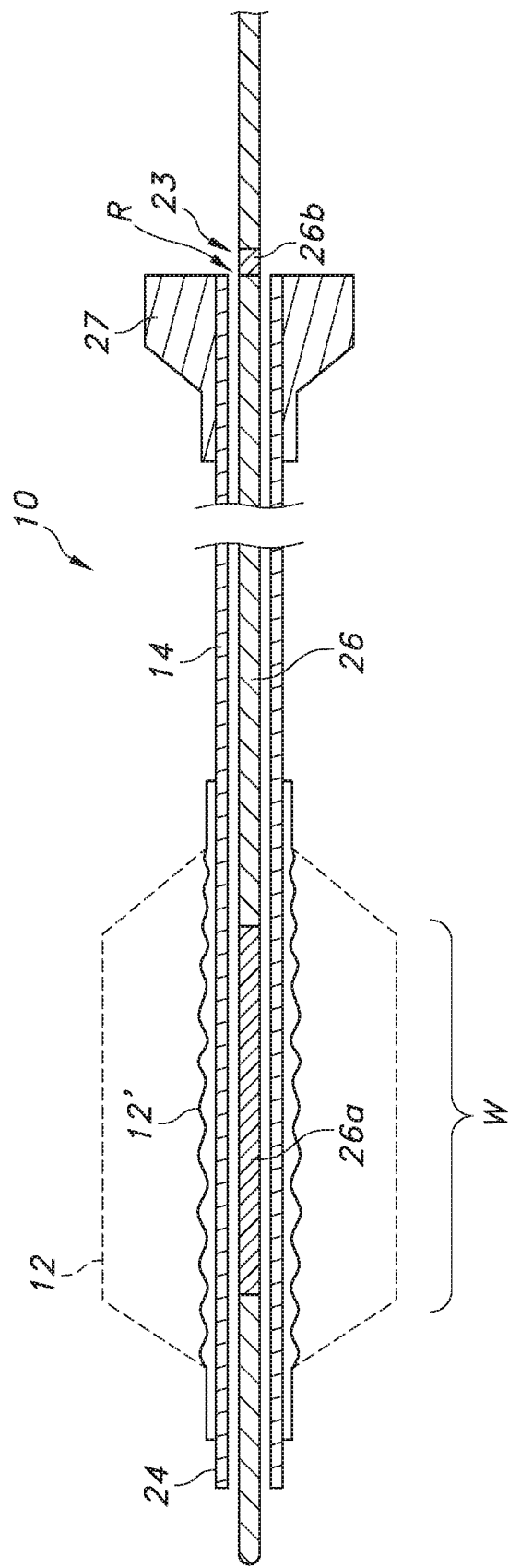
FIG. 4 shows a detail of the apparatus of FIG. 1.

In order to provide for enhanced locatability during an interventional procedure, the guidewire 26 may include one or more radiopaque markings 26a corresponding to and adapted to align with the working surface W of the balloon 12 when inflated. For example, as shown in Figure 4, at least one distal radiopaque marking 26 may be provided at or along a distal portion of the guidewire 26 that corresponds to this working surface W (which in turn corresponds with the treatment area, not shown) of the inflated balloon 12 (as contrasted with the deflated or folded balloon 12'). A second marking 26b may also be provided proximally for corresponding with a reference point R at the proximal end of the catheter 10, such as at the entrance of the guidewire lumen 23 of the connector 27 (hub). This marking 26b thus remains external to the body at all times during the intended use. From FIG. 4, it is clear to the skilled person that the second marking 26b will be provided so as to be outside a patient's vasculature when the device is put to use. Put differently, it will be provided close enough to the proximal end of the catheter such that during surgery, the marking will not be within the patient's body. It is also clear to the skilled person from FIG. 4 that the second marking 26b will be visible by the naked eye.

Figure 5:
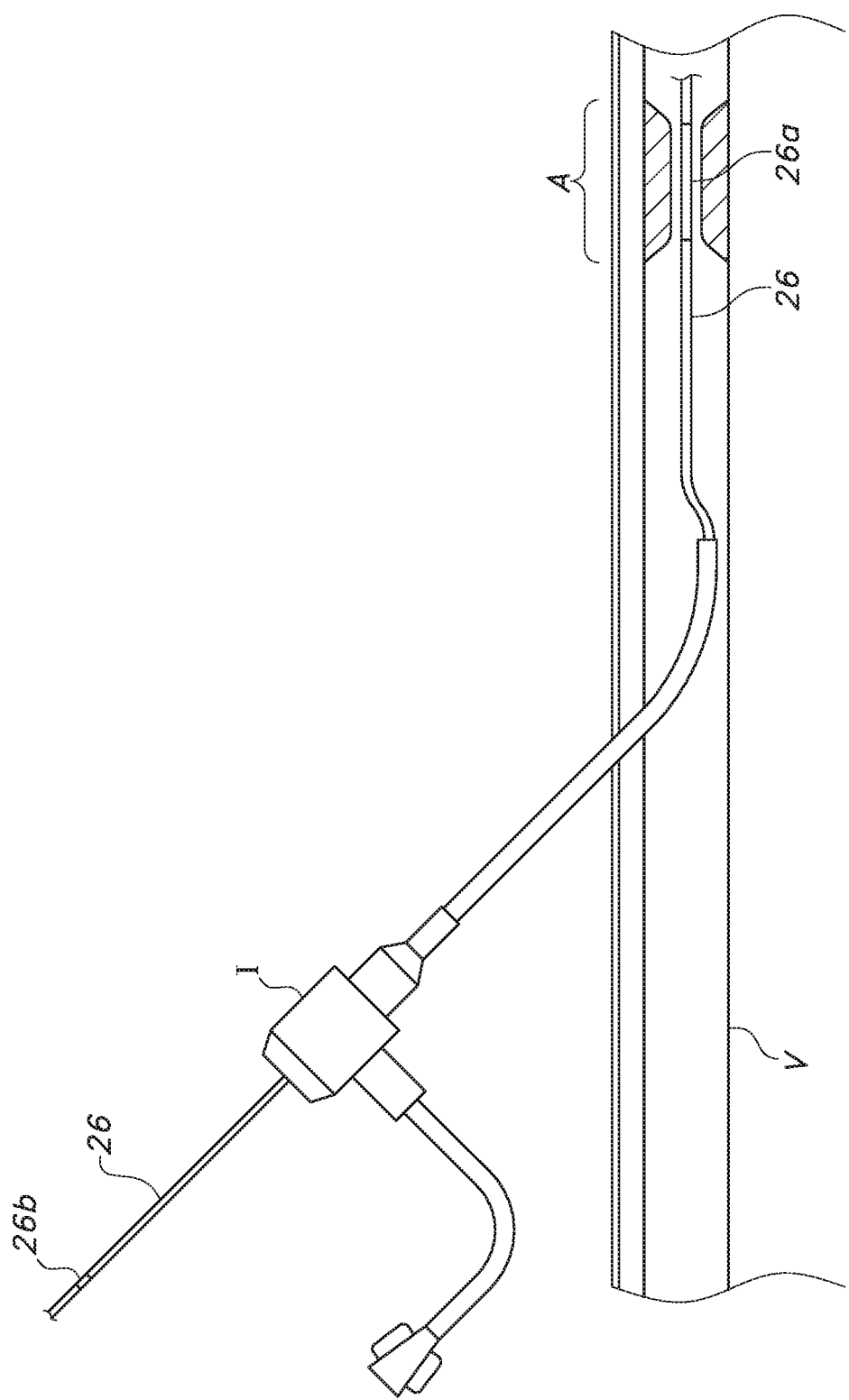
FIGS. 5 and 6 show a way in which the embodiment shown in FIGS. 1-4 can be used.

In practice, the guidewire 26 may be positioned at a treatment area A within a vessel V, as shown in FIG. 5, such as by using a device called an introducer I. For instance, the positioning may be such that one or more of the radiopaque markings 26a align with the treatment area A in a predetermined manner, or alternatively, the location of the treatment area A relative to the markings 26a may be noted. As should be appreciated, the proximal marking 26b remains outside of the body and, hence, the vessel V, at all times.

A catheter 10 including a balloon 12 may then be co-located with the guidewire 26 by aligning a reference point R, such as the entrance of the guidewire lumen 23 on connector 27, with the marking 26b. As the distance between the reference point R and the working surface W of balloon 12 correspond precisely to the distance between the markings 26a, 26b of the guidewire 26, proper alignment is assured. Furthermore, if the catheter 10 is removed and replaced with a second catheter of substantially identical geometry, alignment would again be assured. This advantageously helps to reduce the chances of geographic misalignment between the working surface W and the treatment area A, especially during subsequent interventions. It may also avoid the need for providing any radiopaque markers, such as bands, on the catheter 10 itself.

Figure 6:
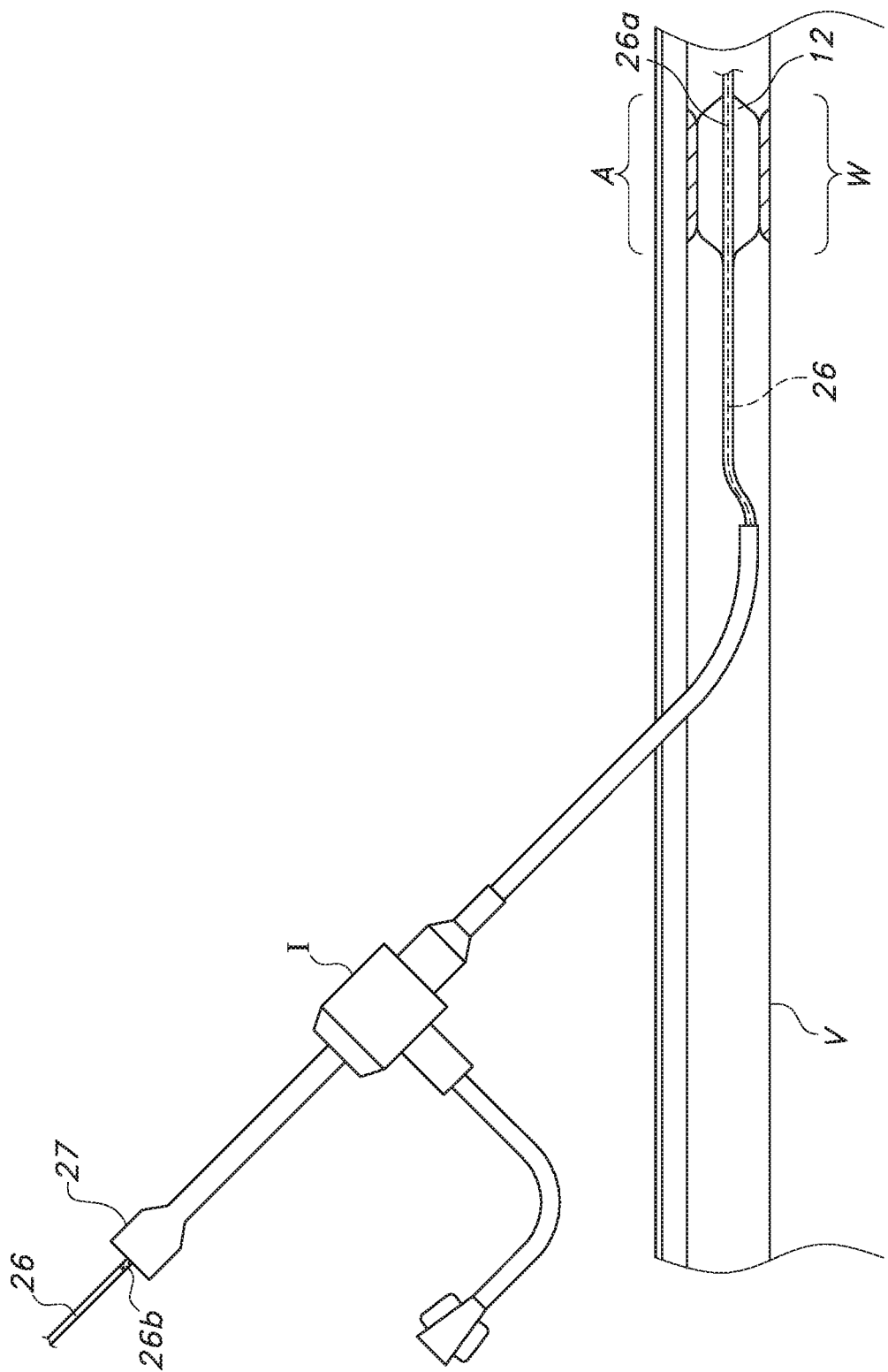

FIGS. 7-10 illustrate various ways in which the one or more radiopaque markings 26a may be provided on the guidewire 26. FIG. 7 illustrates one such marking 26a as shown in FIGS. 4-6, which in use spans the full length of the working surface W of a particular size catheter 10. FIGS. 8 and 9 illustrate two markings 26a bounding the portion of the guidewire 26 corresponding to the treatment area A. FIG. 10 illustrates that a plurality of substantially equally spaced markings 26a may be provided along the portion of the guidewire 26 corresponding to the treatment area A.

Figure 11:
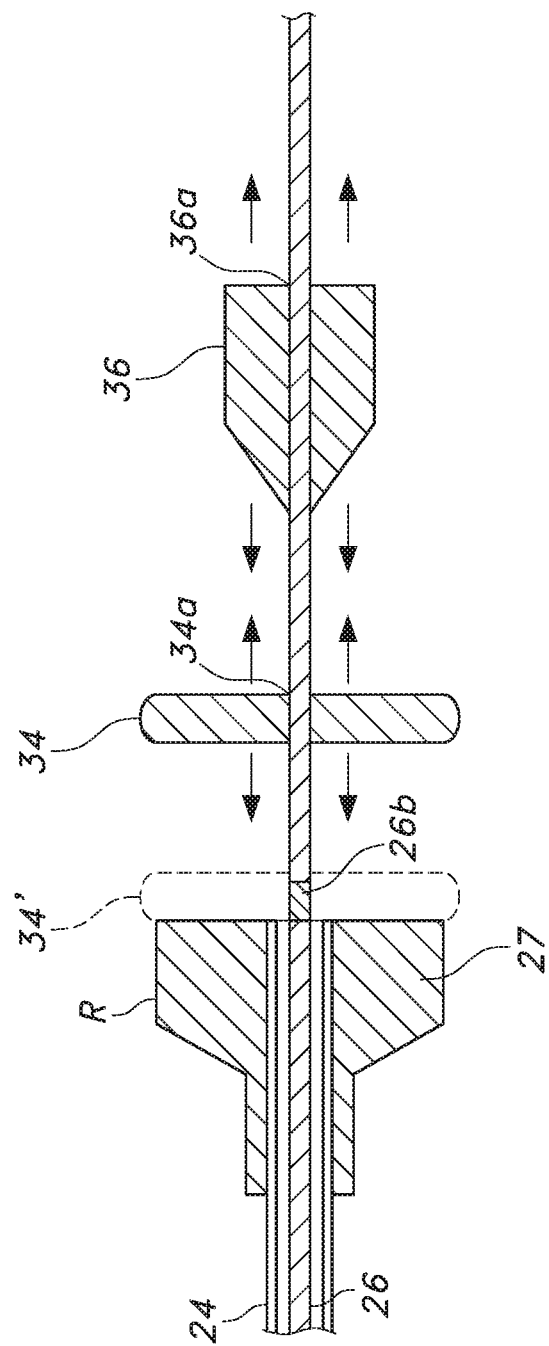
FIG. 11 shows two stoppers to be used with a guidewire used in an embodiment of the present disclosure.

An optional device may be used to retain the guidewire 26 in the desired position. FIG. 11 shows this device as two independent forms of stoppers 34, 36. The first stopper 34 is a disc having a passage 34a for receiving the guidewire 26. This stopper 34 may slide along the properly positioned guidewire 26 into abutment with the proximal face of the connector 27 adjacent the reference point R (note position of stopper 34'). Alternatively, a stopper 36 in the form of a "bullet" may be used with a frusto-conical or tapered distal end for entering the guidewire tube 24 (the guidewire 26 may slide through a corresponding passage 36a). These stoppers 34, 36 may be fabricated of a resilient material, such as silicone rubber, and thus provide a sufficient frictional gripping force on the guidewire 26 to prevent it from slipping once the relative position is determined. Multiple stoppers may also be provided to achieve this result.

Figure 12:
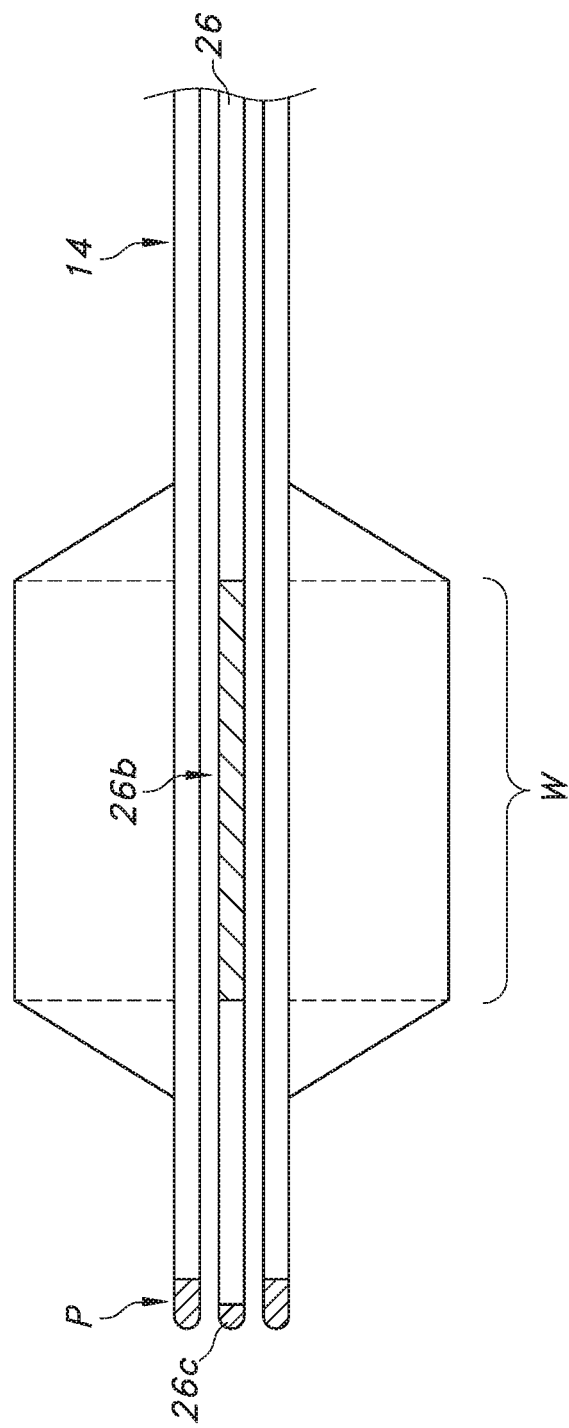
FIG. 12 shows a tip marking on a guidewire used in an embodiment of the present disclosure.

The radiopaque markings 26a can also be aligned with the working surface W of the balloon 12 by placing a radiopaque identifier or marking on the distal end or tip of the guidewire, such as at the tip marking 26c as shown in FIG. 12. When the distal tip of the guidewire 26 is aligned with the distal tip P of the catheter 10, which may also be made radiopaque, the radiopaque marking or markings 26a align with the working surface W of the balloon 12. A radiopaque marking 26c on the tip on the guidewire 26 may be provided by affixing a small length of a radiopaque metal to the distal end of the wire by swaging, welding, soldering, adhesive bonding, or other mechanical means.

In addition to the radiopaque marking or markings 26a associated with the working surface W, another possibility as shown in FIG. 13 is to place another radiopaque marking 26d on the guidewire 26 at a location proximal of the balloon 12. In conjunction with this, a radiopaque marking 40 could be provided on the catheter 10, such as on shaft 14. Consequently, when this radiopaque marking 26d aligns with the radiopaque marker 40 on the catheter shaft 14, the radiopaque markings or markings 26a align with the working surface W of the balloon. Variations of this concept may include multiple radiopaque markings 26e, 26f on the wire 26 which align with a single marking 40 on the shaft 14 (FIG. 14), or multiple radiopaque markings 40, 42 on the shaft 14 with align with a single marking 26d on the wire 26 (FIG. 15). Any other combination of multiple markings that may align are also envisioned.

The one or more radiopaque markings 26a-26f of the guidewire 26 may be provided in a variety of ways. They may be formed as integral parts of the wire, or may be separately attached (including by bonding, welding, soldering, brazing, winding, coating, or like processes). Specific examples include forming the wire 26 by winding a highly radiopaque winding wire of platinum, gold, or tungsten about a central core wire, applying a radiopaque ink to the wire, bonding a radiopaque sleeve to the wire, such as a tungsten filled polymer sleeve, or affixing a series of small radiopaque metal bands to the wire. The markings 26a may be provided as radiopaque portions of the wire 26 interposed with non-radiopaque portions, or the markings 26a may comprise radiopaque portions of the wire 26 that have a different radiopaque quality as compared to other portions of the wire. The marking 26b, which need not be radiopaque, may be formed by printing, painting, coating, bonding, or like processes.

While the disclosure presents certain embodiments to illustrate the inventive concepts, numerous modifications, alterations, and changes to the described embodiments are possible without departing from the sphere and scope of the present invention, as defined in the appended claims. Any ranges and numerical values provided in the various embodiments are subject to variation due to tolerances, due to variations in environmental factors and material quality, and due to modifications of the structure and shape of the balloon, and thus can be considered to be approximate and the term "approximately" means that the relevant value can, at minimum, vary because of such factors. Also, the drawings, while illustrating the inventive concepts, are not to scale, and should not be limited to any particular sizes or dimensions. Accordingly, it is intended that the present disclosure not be limited to the described embodiments, but that it has the full scope defined by the language of the following claims, and equivalents thereof.

The invention claimed is:

1. An apparatus for treating a treatment area along an inner wall of a vessel using a catheter having a balloon including a working surface, the working surface being a surface along a largest diameter portion of the balloon adapted to contact the treatment area within the vessel when the balloon is inflated, comprising:
   a guidewire for guiding the balloon to the treatment area, said guidewire including one or more radiopaque markings corresponding to a length of the working surface of the balloon, the correspondence being a correspondence in size.

2. An apparatus for treating a treatment area along an inner wall of a vessel, comprising:
   a catheter including a distal end supporting a balloon having a working surface, the working surface being a surface along a largest diameter portion of the balloon adapted to contact the treatment area when the balloon is inflated and a proximal end; and
   a guidewire for guiding the balloon to the treatment area, said guidewire including one or more radiopaque markings adapted for corresponding to a length of the working surface of the balloon when positioned at the treatment area.

3. The apparatus of claim 2, wherein the one or more radiopaque markings correspond in size to the working surface length.

4. The apparatus of claim 2, wherein the one or more radiopaque markings correspond in position to the working surface length.

5. The apparatus of claim 2, wherein the guidewire comprises two first radiopaque markings corresponding to the working surface length.

6. The apparatus of claim 2, wherein the catheter includes a radiopaque reference point at the distal end, and the guidewire includes a marking for corresponding to the reference point.

7. The apparatus of claim 2, wherein the proximal end of the catheter includes a hub having a reference point, the hub including an inflation port.

8. The apparatus of claim 2, further including a stopper through which the guidewire passes and slidably mounted to the guidewire for positioning adjacent to an opening at the proximal end of the catheter when the one or more radiopaque markings corresponds to the length of the working surface of the balloon.

9. The apparatus of claim 2, wherein the one or more radiopaque markings are arranged for identifying a boundary of the working surface of the balloon.

10. The apparatus of claim 2, the working surface has first and second ends, and the one or more radiopaque markings correspond to the first and second ends of the working surface.

11. An apparatus for treating a treatment area in the vasculature using a catheter having a balloon including a barrel section having a length for engaging the treatment area, comprising:

a guidewire for guiding the balloon to the treatment area, said guidewire including one or more radiopaque markings corresponding to the length of the barrel section of the balloon, the correspondence being a correspondence in size.

12. An apparatus for treating a treatment area in the vasculature, comprising:

a catheter including a distal end supporting a balloon having a barrel section and a proximal end; and a guidewire for guiding the balloon to the treatment area, said guidewire including one or more radiopaque markings adapted to correspond to a length of the barrel section of the balloon.

13. The apparatus of claim 1, wherein the working surface does not include tapered portions of the balloon.

14. The apparatus of claim 1, wherein the working surface is a barrel section of the balloon.

* * * * *